(12) United States Patent
Loos et al.

(10) Patent No.: US 8,325,879 B2
(45) Date of Patent: Dec. 4, 2012

(54) FILTER ASSEMBLY FOR COMPUTED TOMOGRAPHY SYSTEMS

(75) Inventors: Marinus Antonius Dimphna Maria Loos, Eindhoven (NL); Felix Godfried Peter Peeters, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 212 days.

(21) Appl. No.: 12/809,082

(22) PCT Filed: Dec. 18, 2008

(86) PCT No.: PCT/IB2008/055403
§ 371 (c)(1),
(2), (4) Date: Sep. 27, 2010

(87) PCT Pub. No.: WO2009/083878
PCT Pub. Date: Jul. 9, 2009

(65) Prior Publication Data
US 2011/0033030 A1 Feb. 10, 2011

(30) Foreign Application Priority Data
Dec. 28, 2007 (CN) .......................... 2007 1 0306618

(51) Int. Cl.
*G21K 3/00* (2006.01)
(52) U.S. Cl. ....................................................... 378/156
(58) Field of Classification Search ................ 378/4, 19, 378/156–159
See application file for complete search history.

(56) References Cited

U.S. PATENT DOCUMENTS

| 2,405,444 | A | * | 8/1946 | Moreau et al. ................ 378/158 |
| 3,717,768 | A | * | 2/1973 | Edholm et al. ................ 378/156 |
| 4,288,695 | A | | 9/1981 | Walters et al. |
| 4,399,550 | A | * | 8/1983 | Hauck et al. ....................... 378/5 |
| 4,975,933 | A | | 12/1990 | Hample |
| 6,990,171 | B2 | * | 1/2006 | Toth et al. ......................... 378/16 |
| 2004/0234021 | A1 | * | 11/2004 | Hoffman ............................ 378/4 |
| 2005/0013411 | A1 | * | 1/2005 | Yahata et al. ................. 378/156 |
| 2007/0003005 | A1 | | 1/2007 | Matsuda |
| 2007/0025520 | A1 | | 2/2007 | Thandiackal et al. |
| 2007/0064876 | A1 | | 3/2007 | Hoffman |
| 2007/0116181 | A1 | * | 5/2007 | Arenson et al. ............... 378/156 |

FOREIGN PATENT DOCUMENTS

| EP | 1192901 A1 | 3/2002 |
| EP | 1498908 A2 | 1/2005 |
| JP | 54025689 A | 2/1979 |

* cited by examiner

Primary Examiner — Irakli Kiknadze

(57) ABSTRACT

The invention relates to x-ray filters in a collimator for controlling the energy of an x-ray beam along a projection axis in computed tomography systems. According to the invention, the filter assembly comprises a filter element for attenuating the x-ray beam, and at least a support plate which fixes the filter element. The filter element and the support plate are notch-shaped in the center part of the filter assembly along a direction perpendicular to the projection axis. The design may free space to be used by other collimator parts and further allows use of more than one filter element in a filter assembly for backup purposes. This simplifies replacement of a defective x-ray filter in the field.

20 Claims, 4 Drawing Sheets

FILTER ASSEMBLY FOR COMPUTED TOMOGRAPHY SYSTEMS

FIELD OF THE INVENTION

The invention relates to computed tomography, particularly to x-ray filters for controlling the energy of an x-ray beam in computed tomography systems.

BACKGROUND OF THE INVENTION

Computed tomography (CT) systems typically include an x-ray source collimated to form a fan beam directed through an object to be imaged, i.e. a patient, and received by an x-ray detector array. The x-ray source, the fan beam and the detector array are oriented to be situated within the x-y plane of a Cartesian coordinate system, termed the "imaging plane". The x-ray source and the detector array may be rotated together on a gantry within the imaging plane, around the imaged object, and hence around the z-axis of the Cartesian coordinate system.

In computed tomography systems, a device called collimator is generally used to minimize the x-ray radiation dose a patient receives. One of the ways to achieve this goal is to insert a bowtie-shaped piece of polymer, called "wedge", in the path of the x-ray beam. The wedge, functioning as an x-ray attenuation filter, is generally a synthetic polymer such as Teflon having an x-ray absorption spectral characteristic near that of water and hence the human body. The attenuation filter is intended to compensate for the variation in thickness of the imaged body. The x-rays that pass through the center of the imaged body, normally the thickest part, are least attenuated by this filter, whereas the x-rays that pass through the edges of the imaged body, normally the thinnest part, are more attenuated by this filter. The result of this selective attenuation is that the x-rays impinging on the detectors have a similar energy and are centered midway around the sensitivity of the detector. The attenuation filter may therefore allow use of more sensitive x-ray detectors reducing the range of x-ray energies. Over time, and under continued x-ray exposure, the mechanical characteristics of the polymer change. The x-rays may degrade the polymer, causing it to become brittle. In combination with mechanical stresses, this can cause cracks which introduce discontinuity of the x-ray beams and may thus cause severe image artefacts.

Prior-art document U.S. Pat. No. 4,975,933 discloses a bowtie x-ray filter assembly for dual energy tomography. According to this disclosure, an attenuation filter is mounted to reduce expansion-induced stress. Particularly, the filter element for the attenuation filter is attached to a movable support plate for positioning the filter element within the x-ray beam. The center of the filter element is affixed to the support plate but the ends are attached so as to slide with changes in temperature and thus with changes in the dimensions of the filter element and the support plate.

FIG. 1A is a diagram of an attenuation filter 10 used in the prior art, for example, the attenuation filter as described in U.S. Pat. No. 4,975,933. FIGS. 1B and 1C are a schematic front view and a cross-sectional view, respectively, corresponding to the attenuation filter 10. The attenuation filter 10, e.g. the polymer wedge, is made of a rectangular filter block 12 of Teflon.

Situated in the exposed face (i.e. the face receiving the x-ray beam along axis 11) of the filter block 12 is a saddle notch 14 extending in the center within the filter block 12 but through less than the full width of the filter block 12 so as to leave a supporting wall 16 intact along the path of the projected fan beam of x-ray 18 radiating vertically along axis 11 so that the thickness of the attenuation filter 12 corresponds inversely to the thickness of a typical object being imaged (not shown). The attenuation filter 10 is thinner in its center so as to attenuate x-rays 18 passing through the thickest portion of the imaged object, and thickest at either edge so as to attenuate most x-rays 18 passing without any attenuation on either side of the imaged object. The purpose of the attenuation filter 10 is to equalize, approximately, the intensity of the x-ray 18 received by a CT detector and hence to allow improved detector sensitivity. Generally, the unexposed face of the attenuation filter 10 is attached to a rectangular support plate (not shown), which positions the attenuation filter 10 within the x-ray beam 18.

U.S. Pat. No. 4,975,933 provides a solution to combat the crack introduced by expansion with temperature. The attenuation filter in the prior art is shaped in such a way that a downwardly extending saddle notch is situated in the exposed face of the filter and is centered within the filter block but through less than the full width of the filter block so as to leave a supporting wall intact. Space, which is at a premium on the rotating part of the computed tomography system, is the price of keeping the supporting wall intact. Intactness of the supporting wall will stop any workpiece from moving through the saddle notch and make movement of the attenuation filter relative to a stationary workpiece in a collimator difficult. Furthermore, the solution provided in the prior art cannot combat the crack introduced by centrifugal forces, which is known as a large source of mechanical stress causing cracks in the attenuation filter.

Therefore, there is a need to provide a filter assembly which is improved with respect to the prior-art filter assembly as described above.

OBJECT AND SUMMARY OF THE INVENTION

It is an object of the invention to achieve a filter assembly having a better performance, as compared to the prior-art filter assembly for computed tomography systems.

To this end, the invention provides a filter assembly intended for use in a computed tomography system having an x-ray source for projecting an x-ray beam along a projection axis, said filter assembly comprising:

a filter element for attenuating the x-ray beam and having a center axis parallel to the projection axis;

a first support plate, on which the filter element is mounted, for positioning the filter element within the x-ray beam; wherein the filter element and the first support plate are notch-shaped in the center part of the filter assembly along a direction perpendicular to the projection axis.

By shaping the filter element and the first support plate with a through-notch in the center of the filter assembly along a direction perpendicular to the projection axis, other collimator parts, for example, a sensor, can be easily placed in the space left vacant by the notches. The position of the sensor or the filter assembly can be easily fixed by relative motion between them, without blocking.

In an embodiment, the filter assembly further comprises a second support plate having a shape similar to that of the first support plate and cooperating with the first support plate so as to sandwich the filter element.

In another embodiment, the filter assembly comprises at least one additional filter element and a support plate having a shape similar to that of the filter element and the first support plate, respectively. Furthermore, each filter element is sandwiched by two support plates.

When, in operation, a filter element breaks down and when more than one filter element is used in a filter assembly, it is possible to replace the defective filter element in the filter assembly with a new one in the field by moving the filter assembly along the direction perpendicular to the projection axis so as to place the new filter element in the right position.

In another embodiment, the support plates are shaped in such a way that they completely cover the side surfaces of the attenuation filter facing the support plates. In this way, the bending moments caused by centrifugal forces will only be present on the support plates, rather than on the filter elements.

In a further embodiment, the filter assembly further comprises a fastening means for fastening the support plates. The fastening means comprises spacer bushes for adjusting the distance between the support plates so as to allow deformation of the filter element upon expansion. This is particularly useful in combating the crack introduced by expansion with temperature.

BRIEF DESCRIPTION OF THE DRAWINGS

The above and other objects and features of the present invention will become more apparent from the following detailed description considered in connection with the accompanying drawings, in which.

Identical reference numerals are used to denote similar parts throughout the Figures.

DESCRIPTION OF EMBODIMENTS

Figure 2A:
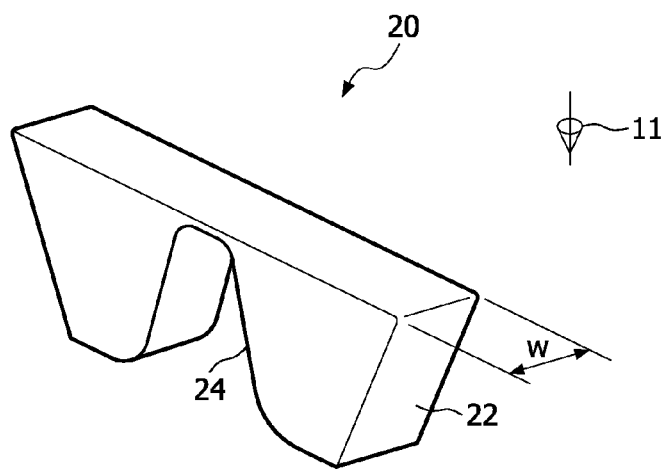
FIG. 2A is a diagram of an embodiment of an attenuation filter 20 according to the invention.
Figure 2B:
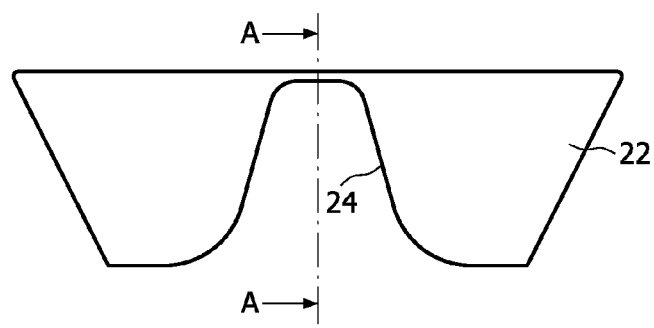
FIG. 2B is a schematic front view of the attenuation filter 20 according to the invention.
Figure 2C:
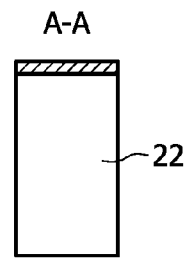
FIG. 2C is a schematic cross-sectional view of the attenuation filter 20, taken on the A-A axis according to the invention.

FIG. 2A is a diagram of an embodiment of an attenuation filter 20 according to the invention; FIGS. 2B and 2C are a corresponding schematic front view and a cross-sectional view, respectively, taken on the A-A axis. The attenuation filter 20 comprises a filter block 22, made of, for example, Teflon. It will be evident to those skilled in the art that other similar materials may be used for the attenuation filter 20. Furthermore, the filter block 22 may have any other shape instead of a rectangular shape, for example, the saddle shape as shown in FIG. 2A.

Figure 1A:
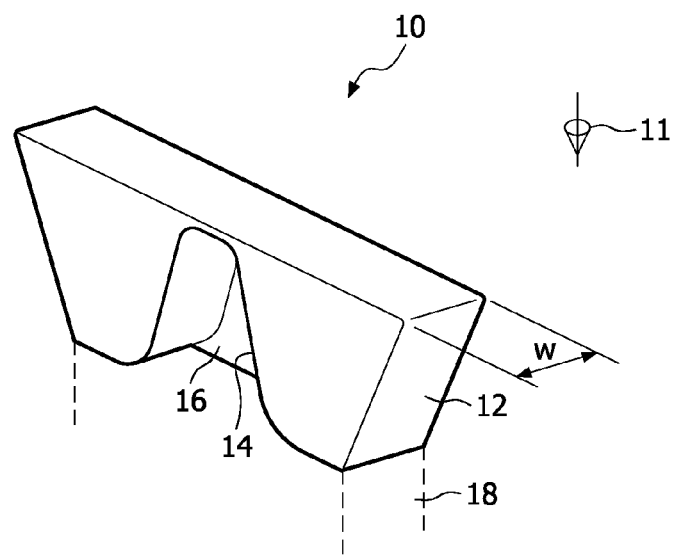
FIG. 1A is a diagram of an attenuation filter 10 of the prior art.
Figure 1B:
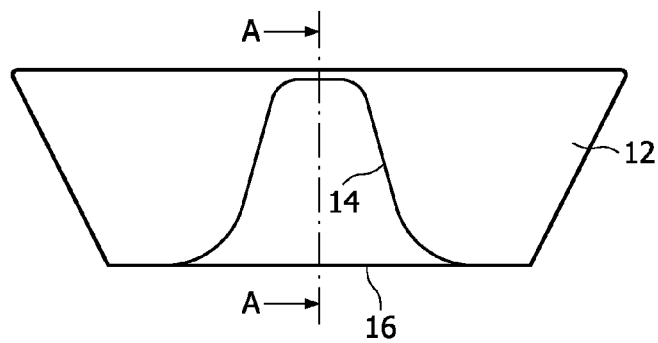
FIG. 1B is a schematic front view of the attenuation filter 10 of the prior art.
Figure 1C:
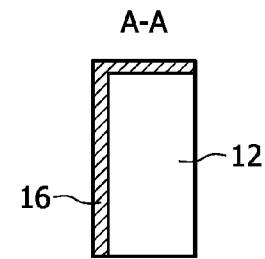
FIG. 1C is a schematic cross-section of the attenuation filter 10 of the prior art, taken on the A-A axis.

The filter block 22 has a saddle-notch shape 24. Unlike the saddle notch 14 in FIG. 1A, the saddle notch 24 is shaped in the full width of the filter block 22 without leaving a supporting wall intact. This means that the saddle notch 24 may allow a workpiece to move through the saddle notch from one to the other side of the attenuation filter 20, or may allow the attenuation filter 20 to freely move relative to a stationary workpiece without blocking, as in the prior-art attenuation filter 10. In this way, the space formed by the saddle notch 24 can be used for placing other collimator parts such as e.g. sensors.

Figure 3:
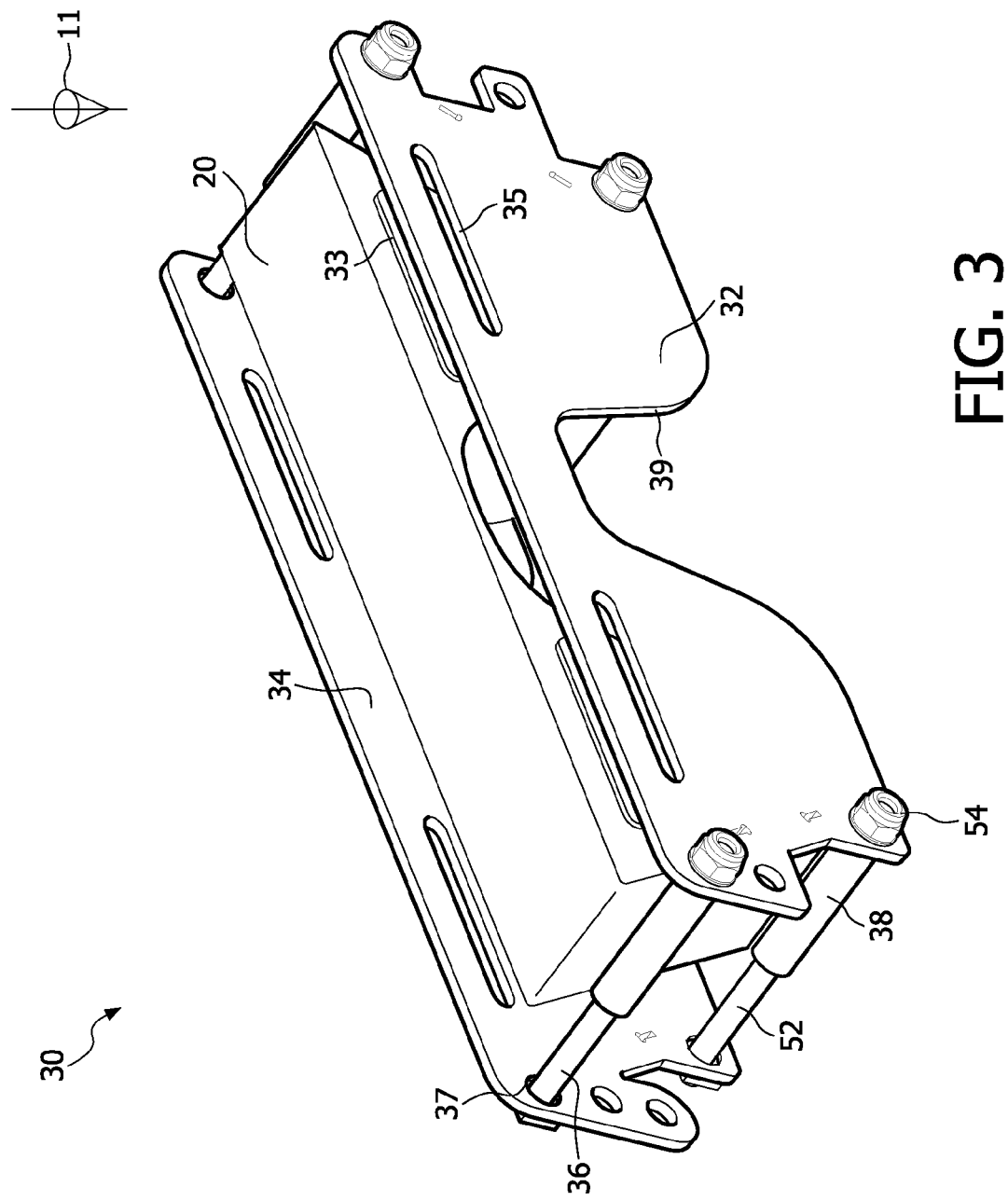
FIG. 3 is a diagram of an embodiment of a filter assembly 30 according to the invention.

FIG. 3 is a diagram of an embodiment of a filter assembly 30 according to the invention. The filter assembly 30 comprises a filter element, corresponding to the attenuation filter 20 as described in FIGS. 2A, 2B and 2C, and a support plate 32, on which the attenuation filter 20 is mounted. The support plate 32 is intended to position the attenuation filter 20 within the x-ray beam. For example, the support plate 32 is made of metal, such as steel, and is thus stiffer and stronger than the attenuation filter 20, which is most likely made of polymer material, for example, Teflon. The attenuation filter 20 comprises protrusions 33 that fit in recesses 35 of the support plate 32. It will be evident to those skilled in the art that the attenuation filter 20 can be mounted on the support plate 32 in other ways. Particularly, protrusions and recesses may have different shapes.

Advantageously, the filter assembly 30 comprises a second support 34 so that the two support plates 32 and 34 sandwich the attenuation filter 20. The support plates 32 and 34 are shaped in such a way that they have similar saddle notches in the center corresponding to the saddle notches in the center of attenuation filter 20, and form a saddle notch 39 through one side to another side in the center part of the filter assembly along a direction perpendicular to the projection axis. This renders it possible to shape the support plate in the saddle notch because of the strength and stiffness of the plate material. This arrangement allows a workpiece to move through from one to the other side of the filter assembly 30, along a direction perpendicular to the projection axis 31. This provides a collimator having more than one attenuation filter.

Furthermore, the support plates 32 and 34 are shaped in such a way that they may completely cover the side surfaces of the attenuation filter 20 facing the support plates, e.g. the side surfaces will not be outwardly exposed. In this way, centrifugal forces will result in forces on the filter at the position of the protrusions, and bending moments will be present in the stiff and strong metal plates, rather than in the polymer of the filter.

Advantageously, the filter assembly 30 further comprises a fastening means 36 for fastening the two support plates, which are mounted together, so as to form a cassette which can be easily exchanged in the field, for example, during maintenance of the tomography system.

The fastening means 36 may comprise lead screws 52 and screw caps 54. The lead screws 52 traverse the holes 37 on the support plates 32 and 34 and are fastened by screw caps 54 at the end of the lead screws 52, which results in the support plates 32 and 34 being attached so as to form a cassette.

Advantageously, the fastening means 36 further comprises spacer bushes 38 which are coupled with the lead screws 52 as shown in FIG. 3 and may adjust the distance between the support plates so as to allow deformation of the polymer upon expansion. This is particularly useful in combating the crack introduced by expansion with temperature.

Figure 4:
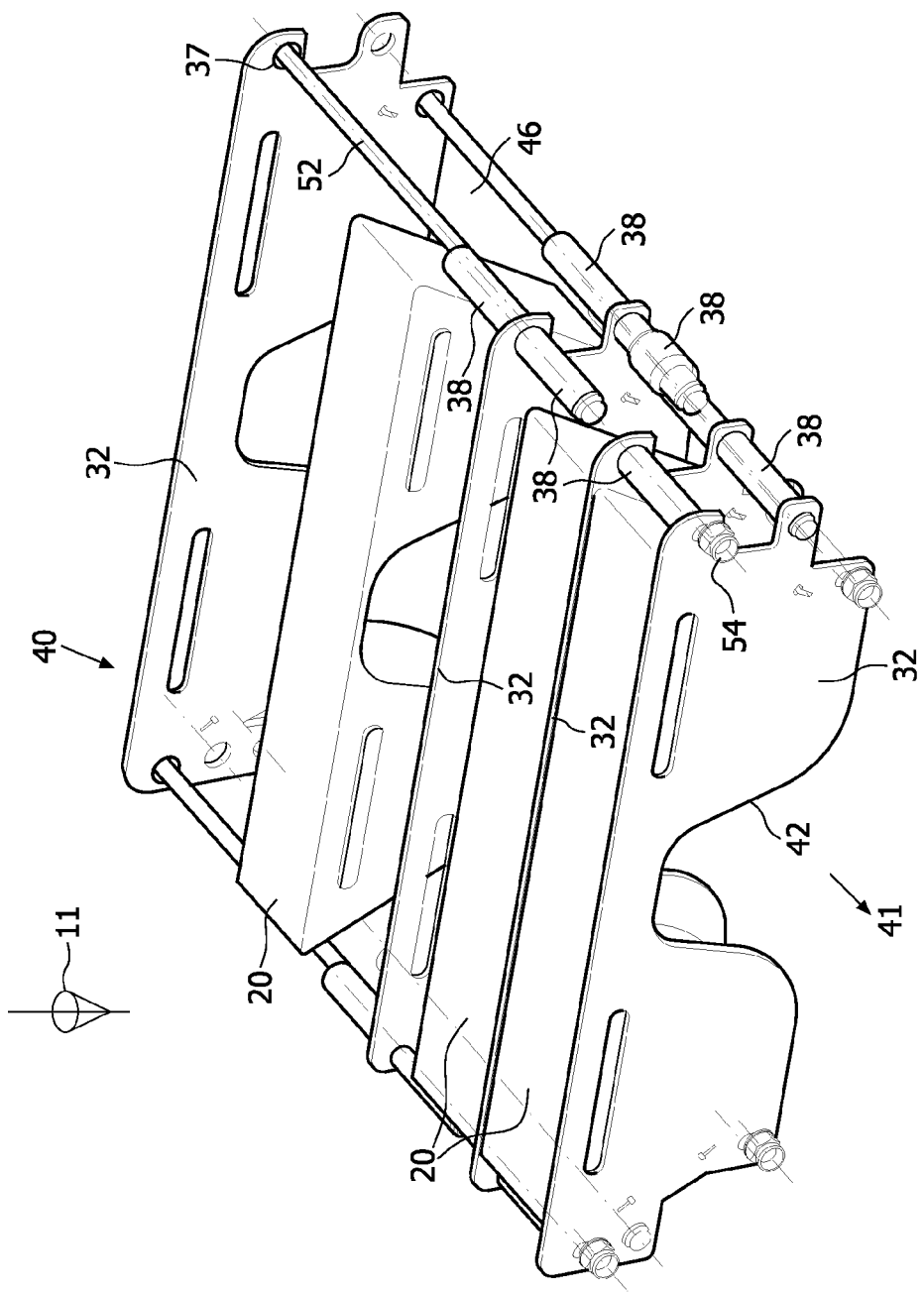
FIG. 4 is a diagram of an embodiment of a filter assembly 40 according to the invention.

FIG. 4 is a diagram of an embodiment of a filter assembly 40 according to the invention. The filter assembly 40 comprises multiple attenuation filters 20, multiple support plates 32 and fastening means 46 that form a cassette. The main difference between the filter assembly 30 and the filter assembly 40 is that the filter assembly 40 has more than one attenuation filter 20 in a cassette.

In an embodiment, each attenuation filter is sandwiched by two support plates, which are connected to other support plates by the fastening means 46, which may comprise, for example, lead screws 52, screw caps 54 and spacer bushes 38, similarly as in FIG. 3. Like the filter assembly 30 described above, the attenuation filters 20 and support plates 32 are shaped in such a way that the filters and support plates form a saddle notch 24 and 42, respectively, in the center of the cassette. This allows a workpiece, for example, parts of a collimator, e.g. a sensor, to freely move through in the space formed by the saddle notch, without blocking along the direction 41 perpendicular to the projection axis 11.

When the filter assembly 30 is in operation, one of the attenuation filters 20 in a cassette is positioned in the x-ray beam and the center axis of the attenuation filter will be parallel to the projection axis 11 of an x-ray source. If a stationary sensor of the collimator is in place, the cassette carrying attenuation filters may also move relative to the sensor for the purpose of positioning.

In case the operating attenuation filter has some defect or breaks down, the defective attenuation filter is to be replaced by another attenuation filter in the cassette by moving the cassette along the direction 41 perpendicular to the projection axis 11 so as to position the attenuation filter in the x-ray beam. In this way, the operator of the tomography system can give instructions for placing an attenuation filter having the same or a slightly differently shape in the beam without having to exchange the cassette. This provides the possibility of replacing attenuation filters in the field and thus greatly simplifies maintenance.

It will be evident to those skilled in the art that the saddle notch in the center of the attenuation filter or support plates may have various shapes, for example, a wedged or a concave shape. Furthermore, the shape of the support plates may also slightly differ from that of the attenuation filter.

It should be noted that the above-mentioned embodiments illustrate rather than limit the invention and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim or in the description. Use of the indefinite article "a" or "an" preceding an element does not exclude the presence of a plurality of such elements. The invention can be implemented by means of hardware comprising several distinct elements. In the system claims enumerating several units, several of these units can be embodied by one and the same item of hardware or software. Use of the words first, second and third, etc. does not indicate any ordering. These words are to be interpreted as names.

The invention claimed is:

1. A filter assembly intended for use in a computed tomography system having an x-ray source for projecting an x-ray beam along a projection axis, said filter assembly comprising:
   a filter element for attenuating the x-ray beam and having a center axis parallel to the projection axis;
   a first support plate, on which the filter element is mounted, for positioning the filter element within the x-ray beam; wherein the filter element and the first support plate are notch-shaped in the center part of the filter assembly along a direction perpendicular to the projection axis; and
   a second support plate having a shape similar to that of the first support plate and cooperating with the first support plate so as to sandwich the filter element(20).

2. The filter assembly as claimed in claim 1, further comprising at least one additional filter element and a support plate having a shape similar to that of the filter element and the first support plate, respectively.

3. The filter assembly as claimed in claim 2, wherein each filter element is sandwiched by two support plates.

4. The filter assembly as claimed in claim 2, wherein the support plates are shaped in such a way that they completely cover the side surfaces of the filter element facing the support plates.

5. The filter assembly as claimed in claim 4, wherein the notch is a saddle notch.

6. The filter assembly as claimed in claim 4, further comprising a fastening means for fastening the support plates so as to form a cassette.

7. The filter assembly as claimed in claim 6, wherein the fastening means comprises spacer bushes for adjusting the distance between the support plates.

8. The filter assembly as claimed in claim 7, wherein the filter element comprises some protrusions cooperating with recesses placed in the support plates so as to mount the filter element on the support plates.

9. A filter assembly, comprising:
   a filter element for attenuating the x-ray beam and having a center axis parallel to the projection axis;
   a first support plate, on which the filter element is mounted, for positioning the filter element within the x-ray beam; wherein the filter element and the first support plate are notch-shaped in the center part of the filter assembly along a direction perpendicular to the projection axis; and
   at least one additional filter element and a support plate having a shape similar to that of the filter element and the first support plate, respectively.

10. The filter assembly as claimed in claim 9, further comprising a second support plate having a shape similar to that of the first support plate and cooperating with the first support plate so as to sandwich the filter element.

11. The filter assembly as claimed in claim 9, wherein each filter element is sandwiched by two support plates.

12. The filter assembly as claimed in claim 9, wherein the support plates are shaped in such a way that they completely cover the side surfaces of the filter element facing the support plates.

13. The filter assembly as claimed in claim 12, wherein the notch is a saddle notch.

14. The filter assembly as claimed in claim 12, further comprising a fastening means for fastening the support plates so as to form a cassette.

15. The filter assembly as claimed in claim 14, wherein the fastening means comprises spacer bushes for adjusting the distance between the support plates.

16. The filter assembly as claimed in claim 15, wherein the filter element comprises some protrusions cooperating with recesses placed in the support plates so as to mount the filter element on the support plates.

17. A method, comprising:
   attenuating an x-ray beam with a filter element, of a filter assembly, that is sandwiched between two support plates that position the filter element within the x-ray beam, wherein the filter element and the support plates are notch-shaped in the center part of the filter assembly along a direction perpendicular to the projection axis.

18. The method of claim 17, further comprising:
   positioning the filter element within the x-ray beam by positioning the two support plates within the x-ray beam.

19. The method of claim 17, wherein the filter assembly includes at least one additional filter element and a support plate having a shape similar to that of the filter element and the first support plate, respectively.

20. The method of claim 17, wherein the notch is a saddle shaped notch.

* * * * *